United States Patent
Rothweiler et al.

(10) Patent No.: US 10,575,896 B2
(45) Date of Patent: *Mar. 3, 2020

(54) ELECTROSURGICAL INSTRUMENT HAVING AN ARCUATE ELECTRODE SECTION

(71) Applicant: Aesculap AG, Tuttlingen (DE)

(72) Inventors: Christoph Rothweiler, Donaueschingen (DE); Eugen Herner, Balingen (DE); Christian Huber, Muehlheim (DE)

(73) Assignee: Aesculap AG (DE)

( * ) Notice: Subject to any disclaimer, the term of this patent is extended or adjusted under 35 U.S.C. 154(b) by 221 days.

This patent is subject to a terminal disclaimer.

(21) Appl. No.: 15/696,888

(22) Filed: Sep. 6, 2017

(65) Prior Publication Data

US 2017/0360500 A1    Dec. 21, 2017

Related U.S. Application Data

(63) Continuation of application No. 14/377,352, filed as application No. PCT/EP2013/052329 on Feb. 6, 2013, now Pat. No. 9,867,655.

(30) Foreign Application Priority Data

Feb. 16, 2012 (DE) ........................ 10 2012 101 257

(51) Int. Cl.
*A61B 18/14* (2006.01)
*A61B 90/00* (2016.01)
*A61B 18/00* (2006.01)

(52) U.S. Cl.
CPC ...... *A61B 18/1445* (2013.01); *A61B 18/1442* (2013.01); *A61B 2018/00589* (2013.01); *A61B 2090/035* (2016.02)

(58) Field of Classification Search
CPC .... A61B 2017/2926; A61B 2017/2945; A61B 2018/1462; A61B 2018/1465; A61B 18/1445; A61B 18/1442
See application file for complete search history.

(56) References Cited

U.S. PATENT DOCUMENTS 3,920,021 A   11/1975   Hiltebrandt
4,427,014 A    1/1984   Bel et al.
(Continued)

FOREIGN PATENT DOCUMENTS

CN    201082191 Y    7/2008
CN    101378702 A    3/2009
(Continued)

OTHER PUBLICATIONS

Japanese Office Action dated Aug. 24, 2016 for Japanese Application No. 2014-530246, including English translation, 9 pages.
(Continued)

*Primary Examiner* — Ronald Hupczey, Jr.
(74) *Attorney, Agent, or Firm* — RatnerPrestia

(57) ABSTRACT

An electrosurgical instrument includes mutually movable instrument legs each comprising one or more electrode faces between which tissue can be clamped and treated in electrothermal manner. The movement of the instrument legs relative to each other can be delimited by at least two spacers which are spaced from each other in the longitudinal direction of the instrument legs and act on the instrument legs. At least one electrode face portion subjected to deflection in a closed position of the instrument legs is formed to be bow-shaped, in particular concave, the curvature being contrary to the bending direction to be expected.

12 Claims, 4 Drawing Sheets

(56) References Cited

U.S. PATENT DOCUMENTS

| | | |
|---|---|---|
| 5,222,973 A | 6/1993 | Sharpe et al. |
| 5,258,006 A | 11/1993 | Rydell et al. |
| 5,318,589 A * | 6/1994 | Lichtman ............... A61B 17/29 |
| | | 600/564 |
| 5,891,142 A | 4/1999 | Eggers et al. |
| 6,030,384 A | 2/2000 | Nezhat |
| 6,123,701 A | 9/2000 | Nezhat |
| 6,190,399 B1 | 2/2001 | Palmer et al. |
| 6,770,072 B1 | 8/2004 | Truckai et al. |
| 6,802,843 B2 | 10/2004 | Truckai et al. |
| 7,101,373 B2 | 9/2006 | Dycus et al. |
| 7,160,299 B2 | 1/2007 | Baily |
| 7,306,599 B2 | 12/2007 | Karasawa et al. |
| 8,915,913 B2 | 12/2014 | Fischer et al. |
| 9,055,961 B2 | 6/2015 | Manzo et al. |
| 9,867,655 B2 * | 1/2018 | Rothweiler ........ A61B 18/1445 |
| 10,092,350 B2 | 10/2018 | Rothweiler et al. |
| 2003/0014053 A1 | 1/2003 | Nguyen et al. |
| 2004/0019352 A1 | 1/2004 | Kidooka |
| 2004/0122423 A1 | 6/2004 | Dycus et al. |
| 2004/0162557 A1 | 8/2004 | Tetzlaff et al. |
| 2004/0249374 A1 | 12/2004 | Tetzlaff et al. |
| 2005/0107784 A1 | 5/2005 | Moses et al. |
| 2006/0217709 A1 | 9/2006 | Couture et al. |
| 2006/0271038 A1 | 11/2006 | Johnson et al. |
| 2008/0015567 A1 | 1/2008 | Kimura |
| 2008/0045944 A1 | 2/2008 | Fischer |
| 2008/0056944 A1 | 3/2008 | Nakamura et al. |
| 2008/0215048 A1 | 9/2008 | Hafner et al. |
| 2010/0016857 A1 | 1/2010 | McKenna |
| 2010/0023043 A1 | 1/2010 | Houser |
| 2010/0057084 A1 | 3/2010 | Hanna |
| 2010/0082047 A1 | 4/2010 | Cosgrove et al. |
| 2010/0204698 A1 | 8/2010 | Chapman et al. |
| 2011/0082494 A1 | 4/2011 | Kerr et al. |
| 2011/0184404 A1 | 7/2011 | Walberg et al. |
| 2012/0083784 A1 | 4/2012 | Davison et al. |
| 2012/0101501 A1 | 4/2012 | Hishimura |
| 2012/0150167 A1 | 6/2012 | Fischer et al. |
| 2012/0271346 A1 | 10/2012 | Townsend et al. |
| 2013/0274741 A1 | 10/2013 | Marczyk et al. |
| 2014/0371743 A1 | 12/2014 | Rothweiler |
| 2015/0216544 A1 | 8/2015 | Banfalvi |
| 2015/0257819 A1 | 9/2015 | Dycus et al. |
| 2016/0157930 A1 | 6/2016 | Heard |

FOREIGN PATENT DOCUMENTS

| | | |
|---|---|---|
| CN | 100544681 C | 9/2009 |
| CN | 101522127 A | 9/2009 |
| CN | 103327922 A | 9/2013 |
| DE | 202004009427 U1 | 8/2004 |
| DE | 102004031141 A1 | 1/2006 |
| DE | 69925854 T2 | 5/2006 |
| DE | 69929230 T2 | 8/2006 |
| DE | 202006016837 U1 | 1/2007 |
| DE | 102006042985 A1 | 4/2007 |
| DE | 102007053359 B3 | 6/2009 |
| DE | 1020080083091 A1 | 8/2009 |
| DE | 102008018614 A1 | 10/2009 |
| DE | 102009037614 A1 | 2/2011 |
| DE | 202012100017 U1 | 3/2012 |
| DE | 102012100040 A1 | 7/2013 |
| EP | 0986990 A1 | 3/2000 |
| EP | 1372507 | 1/2004 |
| EP | 1123058 B1 | 12/2005 |
| EP | 1747762 A2 | 1/2007 |
| EP | 1878400 A1 | 1/2008 |
| EP | 1952777 A1 | 6/2008 |
| EP | 1656901 B1 | 9/2009 |
| EP | 2165662 A1 | 3/2010 |
| GB | 1461810 | 1/1977 |
| JP | 2000102545 A | 4/2000 |
| JP | 2002528167 A | 9/2002 |
| JP | 2004524923 A | 8/2004 |
| JP | 2004532676 A | 10/2004 |
| JP | 2006006942 A | 1/2006 |
| JP | 2006528909 A | 12/2006 |
| JP | 2007319683 A | 12/2007 |
| JP | 2008018226 A | 1/2008 |
| JP | 2009509706 A | 3/2009 |
| JP | 2009297503 A | 12/2009 |
| JP | 2010042248 A | 2/2010 |
| JP | 2010051802 A | 3/2010 |
| JP | 2010253278 A | 11/2010 |
| WO | 02080796 A1 | 10/2002 |
| WO | 2002080797 A1 | 10/2002 |
| WO | 2004103156 A2 | 12/2004 |
| WO | 2011018153 A1 | 2/2011 |
| WO | 2011097469 A2 | 8/2011 |
| WO | 2013102602 A1 | 7/2013 |
| WO | 2015197395 A2 | 12/2015 |

OTHER PUBLICATIONS

Chinese Office Action dated Oct. 29, 2015 for Chinese Application No. 201280045066.1 with translation, 21 pages.

German Search Report issued in related German Application No. 10 2011 053 682.5, dated May 18, 2012, 3 pages.

International Search Report issued in related International Application No. PCT/EP2012/068158, dated Nov. 26, 2012, 3 pages.

International Search Report and Written Opinion for International Application No. PCT/EP2015/063284, dated Sep. 11, 2015, 11 pages.

German Search Report for German Application No. 10 2014 108 914.6, dated Mar. 10, 2015, 12 pages. 2.

Japanese Office Action for Japanese Application No. 2014-556987, dated Dec. 13, 2016 with translation, 5 pages.

German Search Report issued in related German Application No. 10 2012 100 040.9, dated Aug. 28, 2012, 6 pages.

International Search report and Written Opinion issued in related International Application No. PCT/EP2012/076945, dated Aug. 30, 2013. 8 pages.

Japanese Office Action with english translation for Application No. 2014-550685, dated Nov. 22, 2016, 7 pages.

German Search Report for German Application No. 10 2012 101 257.1, dated Nov. 28, 2012 with partial translation, 5 pages.

International Search Report and Written Opinion for International Application No. PCT/EP2013/052329, dated May 8, 2013, 13 pages.

Chinese Office Actioin dated Janruary 4, 2016 for Chinese Application No. 201380011277.8 with translation, 12 pages.

European Office Action for European Application No. 13 703 781.8, dated Apr. 28, 2017 with translation, 8 pages.

European Office Action for European Application No. 12 813 879.9, dated May 2, 2017 with translation, 8 pages.

Notice of Allowance for U.S. Appl. No. 14/377,352, dated May 8, 2017, 23 pages.

Non Final Office Action for U.S. Appl. No. 14/370,553, dated Jun. 30, 2017, 25 pages.

Entire patent prosecution history of U.S. Appl. No. 14/377,352, filed Aug. 7, 2014, entitled, "Electrosurgical Instrument Having an Arcuate Electrode Section."

Non Final Office Action for U.S. Appl. No. 15/319,883, dated Jan. 28, 2019, 41 pages.

Chinese Office Action for Chinese Application No. 201580034220.9, dated Nov. 8, 2018 with translation, 11 pages.

Notice of Allowance for U.S. Appl. No. 14/377,352, dated Sep. 13, 2017, 12 pages.

Notice of Allowance for U.S. Appl. No. 14/370,553, dated Jun. 15, 2018, 7 pages.

Korean Office Action for Korean Application No. 10-2014-7025722, dated Oct. 28, 2019, with translation, 11 pages.

Final Office Action for U.S. Appl. No. 15/319,883, dated Oct. 22, 2019, 19 pages.

* cited by examiner

ELECTROSURGICAL INSTRUMENT HAVING AN ARCUATE ELECTRODE SECTION

RELATED APPLICATIONS

This application is a continuation of U.S. application Ser. No. 14/377,352, filed Aug. 7, 2014, which is the U.S. National Phase entry of International Application No. PCT/EP2013/052329, filed Feb. 6, 2013, which claims the benefit of priority of German Application No. DE 10 2012 101 257.1, filed Feb. 16, 2012. The contents of U.S. application Ser. No. 14/377,352, International Application No. PCT/EP2013/052329, and German Application No. DE 10 2012 101 257.1 are incorporated by reference herein in their entireties for all purposes.

FIELD

The present invention relates to an electrosurgical instrument, in particular for laparoscopic operations, as well as to electrodes for such instruments.

BACKGROUND

Following the surgical removal of a hollow vessel portion, e.g. with an intestinal resection due to a tumor having affected a bowel section, the two hollow vessel portions have to be reconnected at their opened ends in such a manner that a continuous pathway is produced. This is referred to as end-to-end anastomosis. As a standard, the two opened ends are reattached to each other with clip suturing devices.

In particular with operations on the small and large intestines, leaky suture connections (suture insufficiency) occur from time to time, which are associated with a serious progress of disease and a high mortality rate, too.

An alternative to stitching the hollow vessel portions is thermofusion technology (TFT). Thermofusion by means of high frequency technology (HF) is based on the denaturation of proteins which are contained in many tissue types. This allows to weld collagen-containing tissue. During the welding process, the tissue is heated up to temperatures above the protein denaturation temperature, and together with the intra- and extracellular matrix is converted into a gel-like state. After compression of the tissue faces, the liquefied tissue cools down to a fused mass, effecting a reliable connection of the tissue.

For the purpose of welding the hollow vessel portions, the tissue grasped between two clamping jaws is exposed to electrical current which flows between electrodes provided on the two clamping jaws.

For preventing the sealing or welding from breaking down, the parameters acting on the tissue have to be detected and controlled. In order to ensure this, a precise control of temperature, pressure, tissue impedance, distance and position is required.

It is desirable to realize a uniform treatment of the tissue which is held between the clamping jaws, so that all zones are reliably reached and no zone is exposed to an excessively high current. To this end, it has to be ensured that the HF electrodes are uniformly spaced from each other and aligned so as to be parallel to each other.

The prior art does not disclose any instruments of suitable size for being used for the above-mentioned hollow vessels and tissue types. With regard to coagulation instruments of smaller size, as shown e.g. in EP 1 747 762 A2, a non-parallel alignment of the HF electrodes occurs during closing the clamping jaws, which is due to the type of construction.

Related state of the art is known from the documents DE 20 2004 009 427 U1 and DE 699 29 230 T2.

The distance between the electrodes can be maintained by spacers which are attached to the clamping jaws. If, however, a higher number of spacers is provided on the clamping jaws, as is shown for instance in EP 1 656 901 B1, EP1 952 777 A1, EP 1 372 507 A1 or US 2004/122423 A1, it is inevitable that the tissue is perforated by the spacers, as it will be compressed under the spacers in the closed state of the clamping jaws such that there will be permanent tissue damage. This has negative effects on the result of the sealing process.

If the contact pressure of the clamping jaws is reduced in order to avoid any perforation of the tissue, and if the tissue is only clamped under the spacers, this leads to an angular deflection of the clamping jaws.

As the spacers are further made from an electrically non-conductive material for avoiding a short-circuit between the HF electrodes, a so-called coagulation shade develops in the vicinity of said spacers, which means that the tissue portions are encapsulated in the vicinity of or under the spacers, hence are not supplied with electrical current or only to an insufficient extent, and an unsatisfactory welding of the vessel portions will occur.

If the number of the spacers is reduced, it is inevitable that the distance between the individual spacers increases. If the clamping jaws are pressed against each other with high contact pressure, the clamping jaws and the electrodes will be bent between the spacers even if stiff materials are used, so that distance of the electrodes is smaller between the spacers than at the spacers. These differences in the distances of the electrodes results in a non-homogenous penetration of the tissue with HF energy.

SUMMARY OF THE INVENTION

The present invention is based on the object to provide an instrument which improves, by means of thermofusion technology, the result of an end-to-end anastomosis of hollow vessels such as small and large intestines, or in general with any tissue connections, and ensures in particular a uniform distance of opposing HF electrodes without causing damage on the tissue.

A further object of the present invention is the provision of electrodes which are suitable for said instrument.

An electrosurgical instrument according to the invention comprises mutually movable instrument legs each comprising one or more electrodes (electrode faces) between which tissue can be clamped and treated in electrothermal manner. The scissor-like movement of the instrument legs relative to each other is delimited by at least two spacers which are spaced from each other in the longitudinal extension of the instrument legs and act on the instrument legs. At least one electrode face portion subjected to deflection in a closed position of the instrument legs is formed to be bow-shaped in the longitudinal direction of the legs and contrary to the bending direction which is to be expected, in particular so as to be concave toward the opposing leg.

The special shape of the electrode(s) can ensure that the distance of the opposing electrode faces, in consideration of the bending load in the closed position of the instrument legs, is substantially of equal size over the entire electrode length and the full electrode face. This design shape of the electrodes also ensures that there is a substantially constant surface pressure of the tissue to be connected. This results in consistent prerequisites for HF surgery, in particular with respect to the tissue impedance. In this way, the quality of the sealed tissue zones can be better monitored as seen from the viewpoint of electrical control. The special design of the electrodes and spacers avoids short-circuits between the electrodes. What is more, the special configuration results in a homogenous distribution of the electric current in the tissue.

Due to the bow-shaped curvature (which is concave with respect to the contact side) of the electrode(s), the distance between the spacers can be enlarged and hence the total number of the spacers can be reduced without running into danger that the electrode faces fall below the minimum spacing.

As already mentioned at the outset, the tissue to be sealed is damaged too much with an excessively high number of spacers, in particular if these are arranged/fixed on the electrode faces. This means that the (nub-shaped) spacers would perforate the clamped tissue. Further, many coagulation shadows are produced.

The electrosurgical instrument according to the invention and the electrodes, according to the invention, of such an electrosurgical instrument provide for an optimum tradeoff between the maximum parallel alignment of the HF electrodes, on the one hand, and a homogenous fusion of the tissue with minimum tissue damage, on the other hand.

Thus, any tissue damages caused by the spacers due to the excessive force impact on the clamped tissue are prevented and a reliable fusion of the individual tissue components is ensured by constant force conditions, the parallel arrangement of the electrodes, the clearly defined distance of the electrodes and the homogenous distribution of electrical current in the tissue. The special shape of the electrodes (i.e. concave with respect to each other) avoids short-circuits between the electrodes and leaks in the sealed tissue layers in particular in the longitudinal center zone of the legs.

This results in consistent prerequisites for HF surgery, in particular with respect to the tissue impedance. In this way, the quality of the sealed tissue zones can be better monitored as seen from the viewpoint of electrical control.

Especially with particularly long instrument legs or those which are centrally supported on actuation levers, it has to be ensured that the electrode faces maintain the desired distance in the middle zone and do not fall below said distance due to bending loads. The bow-shape of the electrodes with a larger spacing in the center portion allows to do without a spacer which would act on the middle portions of the instrument legs, whereby the total number of required (nub-shaped) spacers can be reduced.

According to a further or independent aspect, at least one electrode face portion arranged between the two spacers which are spaced from each other in the longitudinal extension of the instrument legs can be formed so as to be bow-shaped or concave at least in the longitudinal center portion.

This preferably means, on the one hand, that the electrode as a whole or at least its electrode face facing the tissue to be treated, is preformed so as to be bow-shaped (or concave) along its entire longitudinal extension. Due to the bow-shaped preform, the electrode acts as a kind of leaf spring if it is pressed against the opposing electrode, which is pressed into a flat shape by the contact pressure of the instrument leg and in this way achieves the desired parallel alignment with the other electrode.

However, it is sufficient to give the (concave) preform only to those electrode face portions which are subject to a bending load, i.e. the portions between two support points of the electrodes or between two spacers.

The electrode face portion can be preformed according to the bending load to be expected in the closed position of the instrument legs in such a manner that it does not fall below a minimum spacing between the electrode faces which is defined by the spacers in the closed position of the instrument legs.

This ensures that the electrode faces do not fall below the minimum spacing (in fact at no point) which is essential for a uniform penetration with electrical current and that the electrode faces have a substantially equal distance relative to each other over the entire length.

The electrode face portion can be preformed according to the bending load to be expected in the closed position of the instrument legs in such a manner that it will be bent so as to be substantially straight in the closed position of the instrument legs.

This ensures a parallel alignment of the electrode faces relative to each other, in spite of large distances between the spacers in the closed position of the instrument legs.

The electrode face portion can be preformed according to the number and the distances of the spacers as well as according to the elasticity module and the geometrical moment of inertia of the respective instrument leg.

If the instrument legs are pressed against each other in the closed position for gripping and treating tissue, the bending load depends, apart from the number and the distances of the spacers, substantially on the material and geometric properties of the instrument legs which usually have a higher flexural rigidity than the electrodes attached thereon. Against this background, it is reasonable to determine the preform of the electrode faces depending on the characteristics of the instrument legs as a whole.

Instead of only forming the electrode face so as to be bow-shaped, the complete instrument leg along with the electrode face can be formed to be bow-shaped (concave in the sense of the above description).

If the two instrument legs have similar properties (in terms of flexural flexibility), the mutually opposing electrode faces of the instrument legs can be formed to be mirror-symmetric. This facilitates the manufacturing of the electrodes, as they can be used for any of the two instrument legs.

If the spacers act exclusively on proximal and distal end portions of the instrument legs, the entire middle zone of the electrode faces can be formed to be bow-shaped (concave).

This means that the middle zone of the electrodes, which is essential for the treatment of the tissue, can be kept free from any spacers. This avoids tissue damages and coagulation shadows which are induced by the spacers.

The spacer acting on the distal end portions of the instrument legs can be formed by a protrusion which is arranged on a distal end portion of an instrument leg between two electrode faces and points toward the other instrument leg, or by a protrusion which is provided (fixed) on one electrode face or several protrusions which are provided (fixed) on various electrode faces. The spacer acting on the proximal end portions of the instrument legs can be formed by a spacer module (component) which is formed to be separate from the instrument legs and comprises at least one material tongue (tongue platelet) which is clamped between the instrument legs in the closed position, or by the cooperation between at least one rotation limiting pin provided on one of the instrument legs and a guide slot which is formed in the actuation lever and in which the rotation limiting pin is guided.

Due to this special arrangement of the spacers, the electrode faces can be kept free from spacers, whereby the risk of tissue damages and coagulation shadows can be further minimized.

An electrode according to the invention, in particular for an already described electrosurgical instrument is formed to be bow-shaped or concave at least in portions in the longitudinal direction and contrary to a bending direction which is to be expected.

Using an electrode according to the invention in an electrosurgical instrument allows the compensation of any bending loads which are to be expected due to its special (concave) preform during the compression of the legs; in this way, uniform distances between the electrodes are achieved and falling short of minimum distances as well as short-circuits can be avoided.

At a distal end portion and at a proximal end portion, the electrode may comprise one protrusion each which acts as a spacer, in particular made of a non-conducting material, and the electrode between the protrusions can be formed to be bow-shaped or concave.

On the one hand, an electrode of this type ensures in the installed state that two instrument legs keep the minimum spacing relative to each other (predetermined by the protrusions) along the entire length of the legs and, on the other hand, that the minimum spacing is maintained also between the spacers in spite of any bending loads, at least is not less than said minimum spacing.

It is to be noted that the above-mentioned aspects and features both may exist individually and be combined in grouped fashion.

DETAILED DESCRIPTION OF PREFERRED EMBODIMENTS

Figure 1:
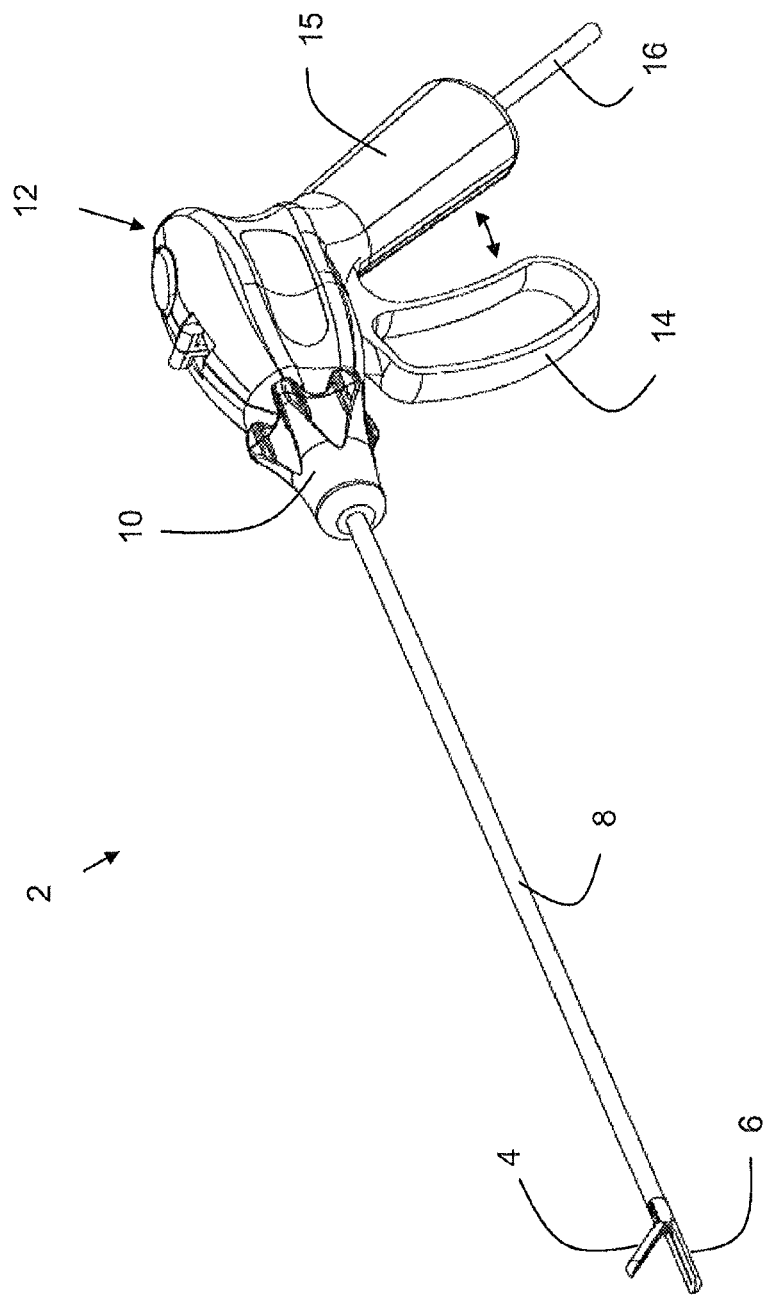
FIG. 1 shows an electrosurgical instrument according to a first embodiment of the invention.

FIG. 1 shows a perspective view of a laparoscopic electrosurgical instrument or of a coagulation clamp 2 according to a first embodiment of the invention comprising a pair of instrument legs 4 and 6 in an open position which are arranged at the distal end of an (instrument) shaft 8 which for its part is rotatably fastened to a manipulation piece or handle piece 12 via a shaft rotation means 10. The shaft rotation means 10 allows to rotate the shaft 8 and the instrument legs 4 and 6 arranged thereon relative to the manipulation piece 12 around the longitudinal axis of the shaft. The manipulation piece 12 comprises an operable handle or trigger 14 which can be moved relative to a second handle (pistol grip) 16 which is firmly connected to the manipulation piece 12. The instrument legs 4, 6, which move in the manner of scissors, are in operative connection with the handle 14 via a (not shown) actuating mechanism, for instance a cable pull or a push rod, and can be shifted from an open position to a closed position (and vice versa) preferably continuously by manually operating the handle 14. By means of a line (which is only shown in part) or an electric cable 16, the manipulation part 12 is connected to a (not shown) HF energy source, in order to be able to apply HF voltage for the electrothermal treatment of tissue between the instrument legs 4 and 6.

Regarding the basic mode of operation and the mechanical structure of the instrument 2, reference is made for instance to the published document WO 2011/097469 A2.

Figure 2:
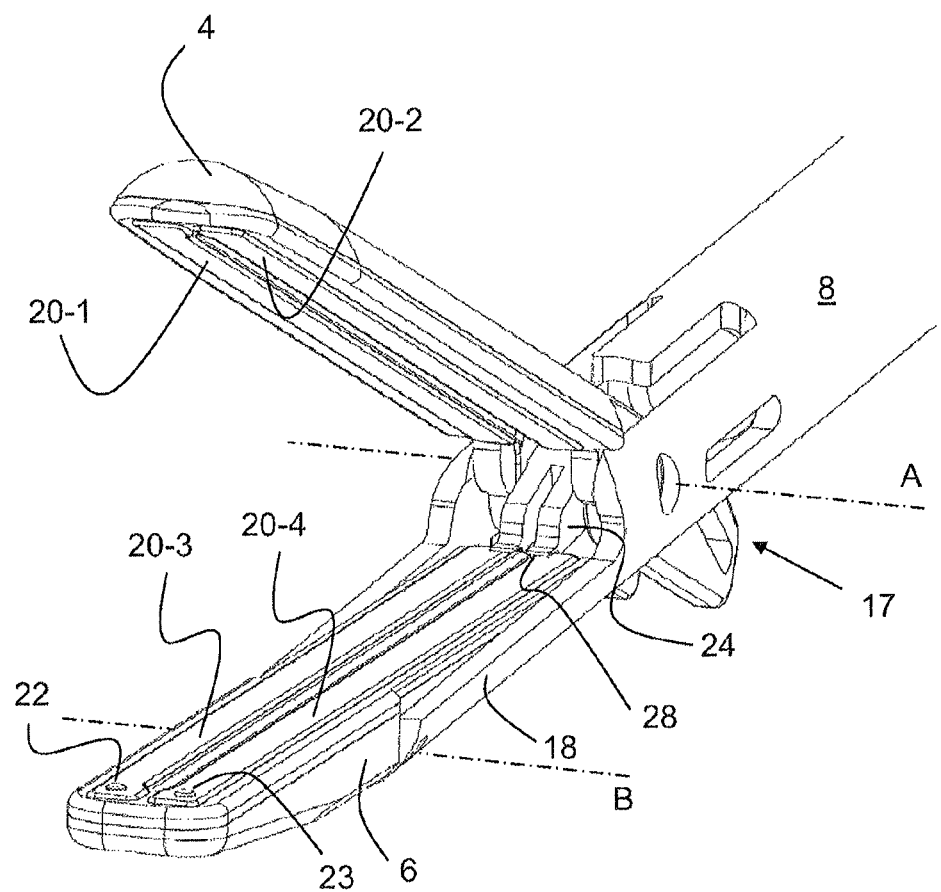
FIG. 2 shows a perspective view of two mutually pivotable instrument legs of the electrosurgical instrument according to the first embodiment of the invention.

FIG. 2 shows only the distal end of the shaft 12 or the instrument jaw part 12 comprising the instrument legs 4 and 6 in an open position. The first instrument leg 4, which is the upper one according to FIG. 2, is supported by a proximal swivel joint 17 on the distal end of the shaft 12 so as to be able to swivel about a transverse axis A. The second or lower instrument leg 6 is partially received in a shell-like support/abutment portion 18 of the shaft 12 which projects beyond the pivot joint 17, and is articulated thereto at its center in the manner of a rocker. A (not shown) spring mechanism (see WO 2011/097469 A2) biases the front (distal) tip of the lower instrument leg 6 in upward direction, i.e. toward the upper instrument leg 4, to facilitate the process of gripping tissue. The lower instrument leg 6 is pivotally supported on the support portion 18 (axis B) only to such an extent that minor angular deviations between the upper and lower instrument legs 4 and 6 can be compensated for in the compressed state.

Each of the instrument legs 4 and 6 comprises two electrode faces 20 (20-1, 20-2, 20-3 and 20-4) which are spaced apart from each other in the transverse direction of the legs, extend parallel in the longitudinal direction and can be supplied with HF voltage. If there is any tissue between the instrument legs 4 and 6 in their closed position, the surgeon is able to coagulate, to sever or to weld it by means of the electrode faces 20. Further, a (not shown) special electrosurgical knife or a cutting device can be arranged between the electrode faces 20.

In order to avoid a short-circuit between the electrode faces 20 of the two instrument legs 4 and 6 and to ensure that a homogenous electrical current (homogenous in the longitudinal direction) flows through the tissue clamped between the electrode faces 20, the electrode faces 20 have to remain preferably equally spaced also in the closed position. To this end, the instrument 2 has its distal portion of at least the lower and/or upper instrument leg 6, 4 on the two parallel electrode faces 20-3 and 20-4 provided with (nub-shaped) protrusions 22 which project beyond the electrode faces 20-3 and 20-4 by a predetermined measure which corresponds to the desired distance between the electrode faces 20, and which come into contact with the corresponding electrode faces 20-1 and 20-2 of the upper instrument leg 4 and in this way act as spacers on the distal end portions of the two instrument legs 4 and 6. These protrusions 22, 23 can be applied by gluing, soldering or injection-molding, or can be applied in any other way so as to be fixed or detachable.

At the proximal portions of the two instrument legs 4 and 6, the distance between the electrode faces 20 is accomplished preferably by a separate spacer module or component 24. This spacer module 24 is a component which is provided/rotatably supported on the pivot joint 17 or forms a part of the pivot joint 17 and is able to freely rotate between the instrument legs 4 and 6 around the swivel axis A. It is received between two hinge flanges of the upper instrument leg 4. It comprises a bearing portion or bearing block provided with two material tongues 28 which extend toward the legs 4, 6, i.e. project radially from the swivel axis A, and whose respective height H (material thickness) corresponds to the minimum spacing S to be achieved between the opposing electrode faces 20-1, 20-3 and 20-2, 20-4, and whose transverse distance and width substantially corresponds to the transverse distance and the width of the electrode faces 20. The spacer module 24 or at least the material tongues 28 are made of an electrically insulating material.

In the closed position (not shown) of the instrument legs 4 and 6, the two material tongues 28 are clamped between the electrode faces 20-1, 20-3 and 20-2, 20-4, whereby the minimum spacing is maintained at the proximal end of the legs 4, 6 between the electrode faces 20-1 and 20-2 on the one side and the electrode faces 20-3 and 20-4 on the other side.

Figure 3:
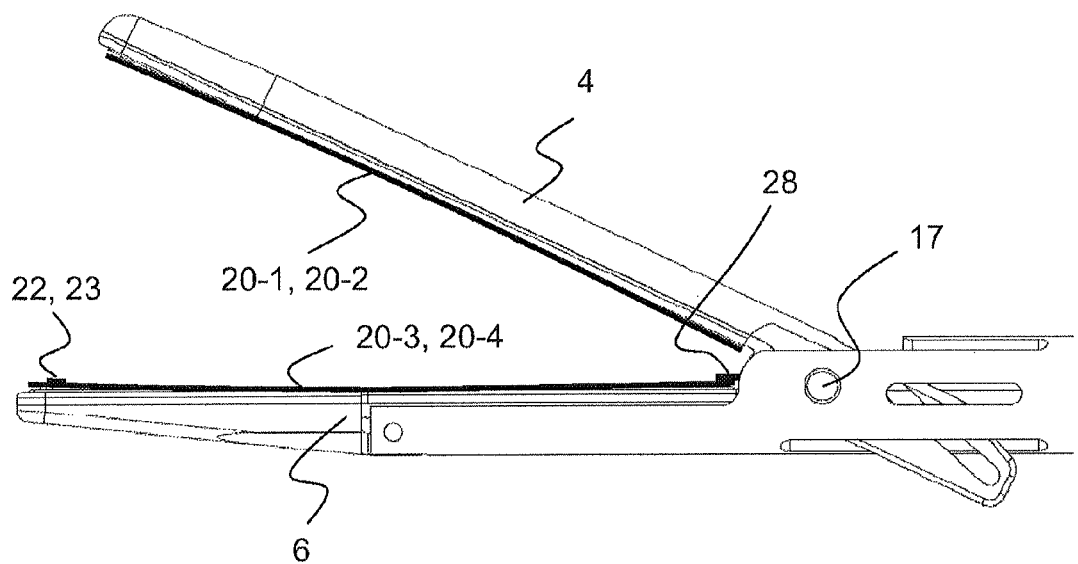
FIG. 3 shows a side view the two instrument legs of FIG. 2 in an open position.

FIG. 3 shows a side view of the two instrument legs 4 and 6 of FIG. 2 in the open position. Although it cannot be clearly seen in FIG. 3, the electrode faces 20-1 and 20-2 of the upper instrument leg 4 and the electrode faces 20-3 and 20-4 of the lower instrument leg 6 each have a slight concave outward curvature over their entire longitudinal extension (the upper electrode faces 20-1 and 20-2 have an upward curvature and the lower electrode faces 20-3 and 20-4 have a downward curvature).

If the instrument legs 4 and 6 are being closed and pressed against each other to carry out an electrothermal treatment on tissue clamped therebetween, the spacers 22, 23 and 24 arranged on the distal and proximal end portions of the instrument legs 4 and 6 come into contact first, as has already been described and is also shown in FIG. 3, which is why the middle portions of the instrument legs 4 and 6 are bent toward each other due to the contact pressure exerted on the instrument legs 4 and 6.

The concave, bow-shaped pretension/preform of the electrodes and electrode faces 20 is selected in each case such that it corresponds to the deflection which is to be expected in the closed position of the instrument legs 4 and 6, i.e. that the electrode faces 20 which are slightly concave in the unloaded state (open position of the instrument legs 4 and 6) are bent so as to be straight or flat in the loaded state (closed position of the instrument legs 4 and 6), which means that the original form of the electrode faces 20 is nullified under bending loads.

Figure 4:
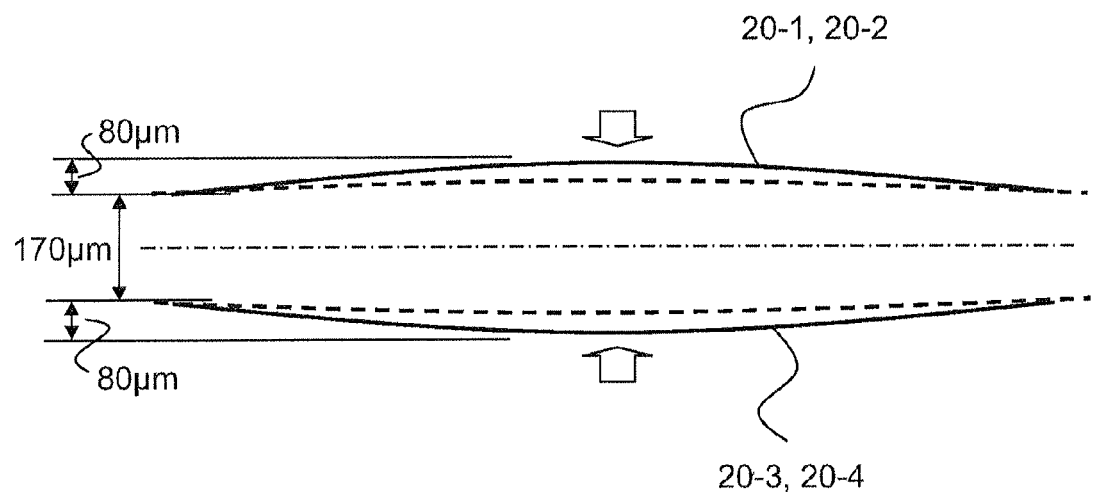
FIG. 4 shows a principle diagram (not true to scale) of two opposing electrodes of the electrosurgical instrument according to the first embodiment of the invention in an unloaded and a loaded state.

FIG. 4 shows a principle diagram, which is not true to scale, of two opposing electrodes 20-1, 20-3 and 20-2, 20-4 of the electrosurgical instrument according to the first embodiment of the invention. The solid lines show the profile of the electrode faces in the unloaded state (open position of the instrument legs 4 and 6 or closed position without any contact pressure), whereas the broken lines illustrate the profile of the electrode faces 20 in the loaded state (closed position with contact pressure).

It can be taken from this sketch that the electrode faces 20 are bent to be straight or flat under bending load, i.e. if the instrument legs 4 and 6 are pressed against each other, so that the upper electrode faces 20-1, 20-2, when the tissue is situated between the instrument legs 4 and 6, and the opposing lower electrode faces 20-3, 20-4 are applied with HF voltage, will have the desired parallel orientation and a substantially uniform distance between them.

Furthermore, FIG. 4 specifies magnitudes of the desired minimum spacing of the electrode faces (approximately 170 μm) during the electrothermal treatment of the tissue and the preliminary bend (height of the arch) of the electrode faces in the straight alignment (approximately 80 μm), which may differ depending on the application and the type of the instrument.

Figure 5:
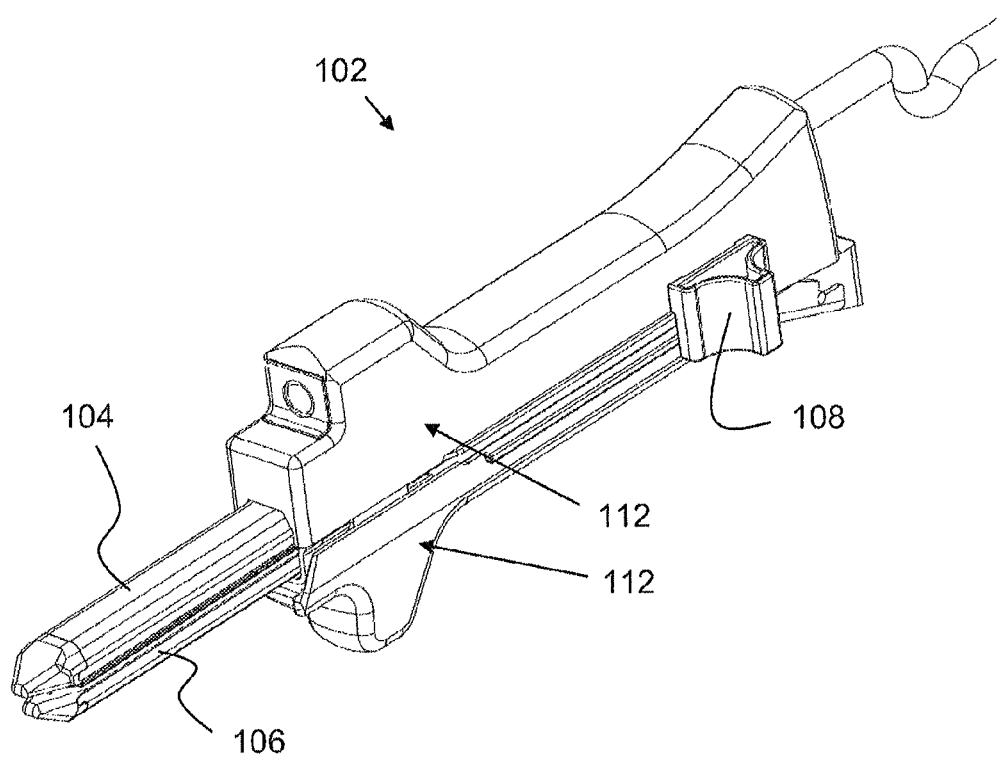
FIG. 5 shows an electrosurgical instrument according to a sixth embodiment of the invention.

FIG. 5 shows an electrosurgical instrument 102 according to a second embodiment, which differs from the instrument 2 described above in terms of the instrument type. Whereas the first embodiment has been described as a laparoscopic electrosurgical instrument 2 comprising a thin, long shaft 12 and instrument legs 4 and 6 pivotally articulated thereon, the spacer arrangements as well as electrode shapes described above can also be realized in connection with the instrument 102 in which the two instrument legs 104 and 106 are partially and simultaneously retracted according to the present structure in a sort of accommodation duct via a manually operable slide element 108 and a sliding mechanism formed on the handle piece 112, whereby the two legs 104, 106 are folded automatically. Here too, bending forces are applied to the instrument legs 104 and 106 in the closed position according to FIG. 5, which are compensated for by the electrodes or electrode faces having the initial concave shape or, alternatively, by the concavely preformed legs.

The present invention is not limited to the embodiments described above. Various modifications are possible within the scope of the invention.

Instead of the spacer module 24, it is also possible to provide protrusions on the proximal portion of the electrode faces, in analogy to the distal end.

In the described first embodiment, the electrode faces are concavely pre-formed or bent over their entire longitudinal extension. The electrode faces, however, may also be concavely bent only between two adjoining spacers.

Further, it is possible that only the electrode faces 20-3 and 20-4 or the electrodes of the lower instrument leg 6 are pretensioned in bow-shaped fashion, as especially the lower instrument leg 6 is subject to central bending forces, because it is centrally supported or suspended on the support portion 18 in the manner of a rocker.

If the instrument legs are provided with several support points or spacers in the longitudinal extension, the electrode faces 20 may have several bends.

The original form of the electrode faces 20, of the entire electrode or of the entire instrument legs 4, 6 may differ from a concave bow-shape (and may be V-shaped, for instance), or the original form of the individual electrode faces may differ from each other, as long as it is ensured that the electrode faces 20 (of opposing instrument legs 4, 6) which are deformed in the loaded state, i.e. if the opposing instrument legs are pressed against each other, have a substantially uniform distance relative to each other over their longitudinal extension.

If it is to be expected that in the closed position of the instrument legs 4 and 6 the electrode faces 20 are not bent inward but in outward direction, the electrode faces may also have a curvature which is oriented inward, i.e. a convex curvature.

What is claimed:

1. An electrosurgical instrument comprising:
   mutually movable instrument legs attached to at least one handle piece, the instrument legs each comprising at least one or more electrode faces, wherein tissue can be clamped between the electrode faces and treated in an electrothermal manner, the movement of the instrument legs relative to each other being delimited by at least two spacers which are spaced from each other in a longitudinal direction of the instrument legs and act on the instrument legs, wherein at least one portion of one of the electrode faces, which is configured to be subjected to deflection in a closed position of the instrument legs by the respective opposing instrument leg, is formed to be concavely bow-shaped and has a curvature as seen in the longitudinal direction of the instrument legs, the curvature being contrary to a bending direction of said one of the electrode faces which is to be expected in a closed position, wherein at least one instrument leg is partially received in a support/abutment portion, the support/abutment portion projecting beyond a pivot joint, and wherein the at least one instrument leg is articulated to the support/abutment portion at the center of the instrument leg in the manner of a rocker.

2. The electrosurgical instrument of claim 1, wherein said at least one portion of one of the electrode faces is arranged between the at least two spacers.

3. The electrosurgical instrument of claim 1, wherein said at least one portion of one of the electrode faces is preformed according to a bending load to be expected in the closed position of the instrument legs in such a manner that it does not fall below a minimum spacing between two electrode faces which is defined by the at least two spacers in the closed position of the instrument legs.

4. The electrosurgical instrument of claim 1, wherein the said at least one portion of one of the electrode faces is preformed according to a bending load to be expected in the closed position of the instrument legs in such a manner that it will be bent so as to be straight or flat in the closed position of the instrument legs.

5. The electrosurgical instrument of claim 1, wherein the said at least one portion of one of the electrode faces is preformed according to the number and the distances of the at least two spacers as well as according to an elasticity module of the respective instrument leg.

6. The electrosurgical instrument of claim 1, wherein the instrument legs and the one or more electrode faces are all formed to be bow-shaped.

7. The electrosurgical instrument of claim 1, wherein the two of the electrode faces of the instrument legs are mutually opposing electrode faces that are formed to be mirror-symmetric.

8. The electrosurgical instrument of claim 1, wherein the at least two spacers act exclusively on a proximal end portion and a distal end portion of each instrument leg and a middle zone of at least one of the electrode faces electrode faces is formed to be bow-shaped between the proximal end portion and the distal end portion of at least one instrument leg.

9. The electrosurgical instrument of claim 1, wherein the two instrument legs are partially and simultaneously retracted in an accommodation tube.

10. An electrode in combination with an electrosurgical instrument, the electrosurgical instrument comprising mutually movable instrument legs, the instrument legs each comprising one or more electrode faces wherein tissue can be clamped between the electrode faces and treated in an electrothermal manner, the movement of the instrument legs relative to each other being delimited by at least two spacers which are spaced from each other in a longitudinal direction of the instrument legs and act on the instrument legs,
wherein at least one portion of one of the electrode faces, which is configured to be subjected to deflection in a closed position of the instrument legs by the respective opposing instrument leg, is formed to be concavely bow-shaped and has a curvature as seen in the longitudinal direction of the instrument legs, the curvature being contrary to a bending direction of said one of the electrode faces which is to be expected in a closed position, wherein at least one instrument leg is partially received in a support/abutment portion, which projects beyond a pivot joint, and the at least one instrument leg is articulated to the support/abutment portion at a center of the instrument leg in the manner of a rocker.

11. The electrode of claim 10, wherein the at least one electrode face comprises a protrusion at a distal end portion of the at least one electrode face and at a proximal end portion of the at least one electrode face, each protrusion acting as a spacer, the at least one electrode face is formed between the protrusions so as to be bow-shaped between the protrusions.

12. The electrode of claim 10, wherein the electrode as a whole or at least the tissue contact side or tissue contact face associated with the electrode comprises a bending or curvature, the bending or curvature extending contrary to a bending direction which is to be expected in the closed position, so that there will be a straight or flat electrode profile in the closed position.

\* \* \* \* \*